US012810972B2

(12) United States Patent
Tourtellotte et al.

(10) Patent No.: US 12,810,972 B2
(45) Date of Patent: Nov. 24, 2026

(54) SYSTEMS AND METHODS FOR DEMAND AND SUPPLY FORECASTING FOR CLINICAL TRIALS

(71) Applicant: 4G CLINICAL, LLC, Wellesley, MA (US)

(72) Inventors: Edward Alan Tourtellotte, Dover, MA (US); Cedric Cristian Marcel Druck, Rosseignies (BE)

(73) Assignee: 4G CLINICAL, LLC, Wellesley, MA (US)

( * ) Notice: Subject to any disclaimer, the term of this patent is extended or adjusted under 35 U.S.C. 154(b) by 0 days.

(21) Appl. No.: 17/852,259

(22) Filed: Jun. 28, 2022

(65) Prior Publication Data

US 2023/0074272 A1 Mar. 9, 2023

Related U.S. Application Data

(63) Continuation of application No. 16/143,049, filed on Sep. 26, 2018, now Pat. No. 11,398,298.

(Continued)

(51) Int. Cl.
*G16H 10/20* (2018.01)
*G06F 17/28* (2006.01)

(Continued)

(52) U.S. Cl.
CPC ............. *G16H 10/20* (2018.01); *G06F 40/40* (2020.01); *G06F 40/177* (2020.01); *G06F 40/18* (2020.01); *G06F 40/289* (2020.01)

(58) Field of Classification Search
CPC ....... G16H 10/20; G06F 40/40; G06F 40/177; G06F 40/18; G06F 40/289; G06F 16/335; G06F 40/20
See application file for complete search history.

(56) References Cited

U.S. PATENT DOCUMENTS 11,398,298 B2 7/2022 Tourtellote et al.
2006/0143047 A1* 6/2006 Briegs .................... G16H 10/20 707/999.009

(Continued)

FOREIGN PATENT DOCUMENTS

JP 2004-078487 A 3/2004
JP 2006-323864 A 11/2006

(Continued)

OTHER PUBLICATIONS

Abdelkafi, Chedia, et al. "Balancing risk and costs to optimize the clinical supply chain—a step beyond simulation." Journal of Pharmaceutical Innovation 4 (2009): 96-106. (Year: 2009).*

(Continued)

*Primary Examiner* — Maroun P Kanaan
(74) *Attorney, Agent, or Firm* — Greenberg Traurig, LLP

(57) ABSTRACT

Systems and methods for demand and supply forecasting for clinical trials are disclosed. An embodiment of a computer-implemented method may include receiving, by a server from a user, one or more electronic files that contain parameters of a clinical trial, the parameters comprising a quantity of patients, a plurality of sites, and one or more confidence values, calculating, by the server, according to the quantity of patients, a respective demand profile for each of the plurality of sites, calculating, by the server, according to the one or more confidence values, a buffer quantity for each of the plurality of sites, calculating, by the server, a supply plan for the clinical trial according to the demand profiles and the buffer quantities, and transmitting, by the server, the supply plan to the user.

20 Claims, 8 Drawing Sheets

Related U.S. Application Data

(60) Provisional application No. 62/563,283, filed on Sep. 26, 2017.

(51) Int. Cl.

| | |
|---|---|
| ***G06F 40/40*** | (2020.01) |
| *G06F 40/177* | (2020.01) |
| *G06F 40/18* | (2020.01) |
| *G06F 40/289* | (2020.01) |

(56) References Cited

U.S. PATENT DOCUMENTS

| | | | | |
|---|---|---|---|---|
| 2007/0067189 | A1 | 3/2007 | Boris et al. | |
| 2009/0292554 | A1 | 11/2009 | Schultz | |
| 2011/0238438 | A1* | 9/2011 | Houriet, Jr. | G16H 10/20 705/2 |
| 2011/0307267 | A1 | 12/2011 | Young et al. | |
| 2012/0303645 | A1* | 11/2012 | Kulkarni-Puranik | G06F 40/18 707/756 |
| 2015/0286802 | A1* | 10/2015 | Kansara | G16H 10/20 705/3 |
| 2016/0267255 | A1* | 9/2016 | Young | G16H 70/40 |
| 2017/0154168 | A1 | 6/2017 | Tourtellote | |
| 2018/0357389 | A9* | 12/2018 | Warren | G16H 20/10 |

FOREIGN PATENT DOCUMENTS

| | | | |
|---|---|---|---|
| JP | 2013530470 | A | 7/2013 |
| WO | 2012122516 | A1 | 9/2012 |

OTHER PUBLICATIONS

Chen, Ye, et al. "Simulation-optimization approach to clinical trial supply chain management with demand scenario forecast." Computers & Chemical Engineering 40 (2012): 82-96. (Year: 2012).*

Peterson, Magnus, et al. "Optimizing clinical trial supply requirements: simulation of computer-controlled supply chain management." Clinical Trials 1.4 (2004): 399-412. (Year: 2004).*

He, Weili, et al. "Practical considerations and strategies for executing adaptive clinical trials." Drug information journal: DIJ/Drug Information Association 46 (2012): 160-174. (Year: 2012).*

U.S. Appl. No. 16/143,049 U.S. Pat. No. 11,398,298, US20200330275A1, filed Apr. 19, 2014 Jul. 26, 2022 Oct. 22, 2020, Systems and Methods for Demand and Supply Forecasting for Clinical Trials.

PCT International Search Report for International Application No. PCT/US2018/052952 dated Nov. 30, 2018.

Abdelkafi et al., "Balancing Risk and Costs to Optimize the Clinical Supply Chain—A Step Beyond Simulation," Journal of Pharmaceutical Innovation, Sep. 1, 2009, vol. 4, No. 3, pp. 96-106.

Dowlman; Nikki et al. Optimizing the Supply Chain Through Trial Simulation: Jul. 2004, Applied Clinical Trials, vol. 13, No. 7. pp. 40-46. (Year 2004).

Japanese Office Action date Nov. 29, 2024, from related Japanese Patent Application 2023-162936.

* cited by examiner

SYSTEMS AND METHODS FOR DEMAND AND SUPPLY FORECASTING FOR CLINICAL TRIALS

CROSS-REFERENCE TO RELATED APPLICATION

This application is a continuation patent application of U.S. application Ser. No. 16/143,049, filed Sep. 26, 2018, which claims priority to and the benefit of U.S. provisional application No. 62/563,283, filed Sep. 26, 2017, each of which are hereby incorporated by reference in their entireties.

FIELD

The presently disclosed embodiments relate to clinical trial supply and management, and more particularly to systems and methods for demand and supply forecasting for clinical trials.

BACKGROUND

Over the past decade, systems for managing the supply of pharmaceuticals in a clinical trial have been developed and are now a much relied on system for a number of pharmaceutical companies, for production planning, cost optimization, patient recruitment campaigns management and more. For example, known systems include custom or template Excel spreadsheets, average-based forecasting systems, and systems using Monte-Carlo simulations, which are generally the most precise.

SUMMARY

The presently disclosed embodiments relate to systems and methods for demand and supply forecasting for clinical trials. An embodiment of a computer-implemented method may include receiving, by a server from a user, one or more electronic files that contain parameters of a clinical trial, the parameters comprising a quantity of patients, a plurality of sites, and one or more confidence values, calculating, by the server, according to the quantity of patients, a respective demand profile for each of the plurality of sites, calculating, by the server, according to the one or more confidence values, a buffer quantity for each of the plurality of sites, calculating, by the server, a supply plan for the clinical trial according to the demand profiles and the buffer quantities, and transmitting, by the server, the supply plan to the user.

An embodiment of a computer-implemented method may include receiving, by a server from a user, one or more electronic files that contain parameters of a clinical trial, the parameters comprising a quantity of patients, a plurality of sites, and one or more confidence values, calculating, by the server, a supply plan for the clinical trial according to parameters, transmitting, by the server, the supply plan to the user, after transmitting the supply plan to the user, establishing electronic communication with a computerized randomization and trial supply management (RTSM) system that operates the clinical trial, outputting commands to the RTSM system via an application programming interface (API) respective of the RTSM system, receiving data from the RTSM system in response to the commands, determining a status of the clinical trial according to the data received from the RTSM system, comparing the status of the clinical trial to the supply plan, determining that the clinical trial does not conform to the supply plan, and automatically transmitting an electronic notification to the user, the electronic notification comprising an indication that the clinical trial does not conform to the supply plan.

An embodiment of a computer-implemented method may include receiving, by a server from a user, one or more electronic files that contain parameters of a clinical trial, the parameters comprising a quantity of patients, a plurality of sites, and one or more confidence values, wherein the one or more electronic files comprise an electronic spreadsheet file and one or more text files, converting the data in the electronic spreadsheet file into one or more electronic text-based tables, inserting the one or more electronic text-based tables into the one or more text files to create one or more supplemented text files, performing natural language processing on the one or more text files to determine the parameters of the clinical trial, calculating, by the server, a supply plan for the clinical trial according to the parameters of the clinical trial, and transmitting, by the server, the supply plan to the user.

An embodiment of a non-transitory computer-readable medium may store instructions that, when executed by a processor, cause the processor to receive, from a user, one or more electronic files that contain parameters of a clinical trial, the parameters comprising a quantity of patients, a plurality of sites, and one or more confidence values, calculate, according to the quantity of patients, a respective demand profile for each of the plurality of sites, calculate, according to the one or more confidence values, a buffer quantity for each of the plurality of sites, calculate, by the server, a supply plan for the clinical trial according to the demand profiles and the buffer quantities, and transmit the supply plan to the user.

DETAILED DESCRIPTION

Figure 1:
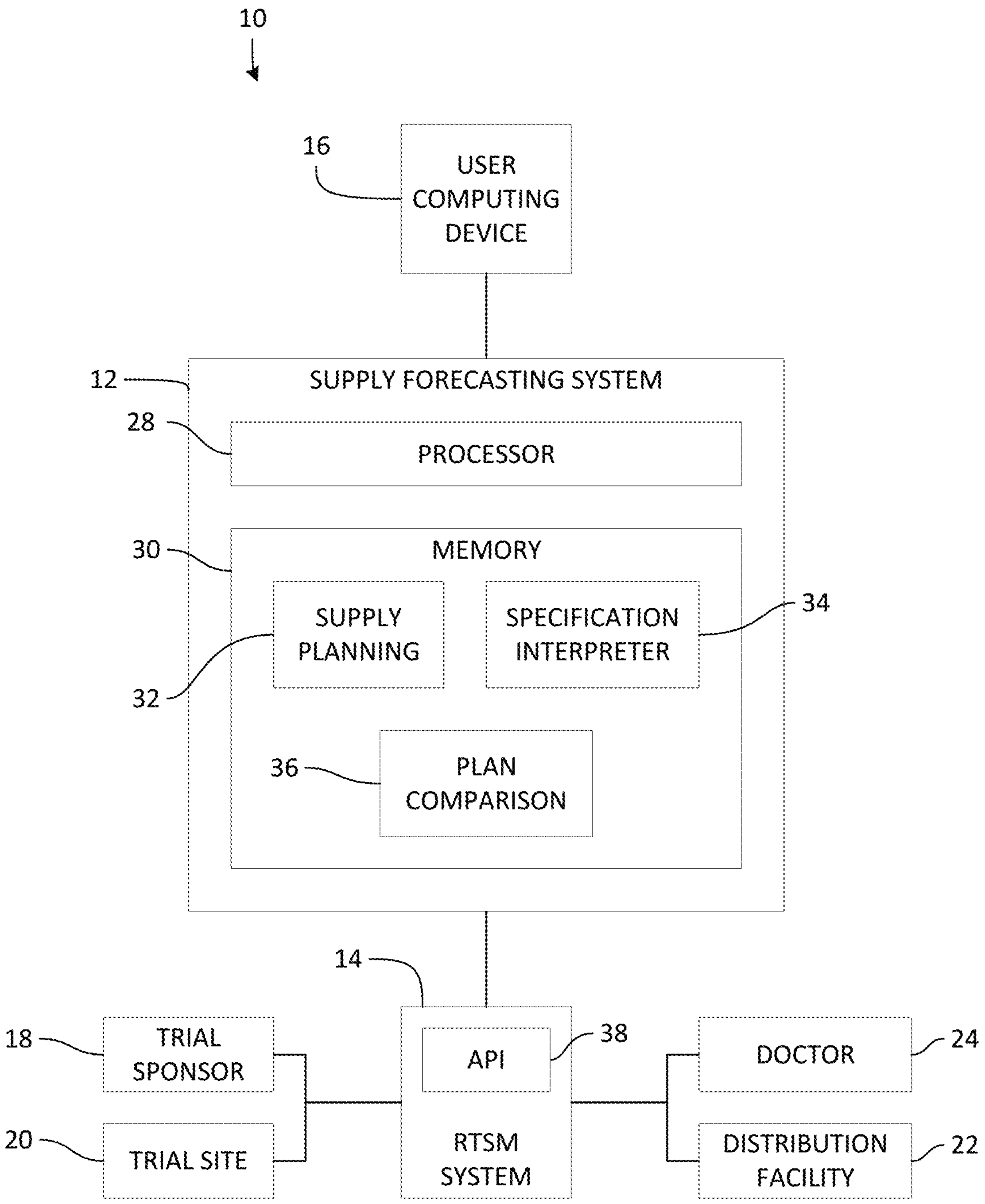
FIG. 1 is a diagrammatic view of an example system for forecasting and managing a pharmaceutical trial.

RTSM systems may predict demand of clinical supply at investigative sites where patients are participating in clinical trials, to pre-seed those sites with appropriate drug for dispensing, and to send additional drug to those sites when required. This function is typically called a "resupply algorithm." Resupply algorithms can be controlled by parameters such as minimum levels or safety stock, maximum levels or resupply levels, short-windows, look-ahead windows, and more. The management of these parameters—calculating projected parameter values across the world in a given clinical trial, then tracking and updating those values—is a burden for pharmaceutical companies.

In the past decade, forecasting tools have been developed in order to help plan supply needs in advance, and also to tune resupply parameters (and get a view of what is coming) in an ongoing basis in a clinical trial. Existing forecasting systems have numerous shortcomings. Some of these forecasting tools use simulation techniques as the backbone of their forecasting power. Since forecasting tools need to approximate the behavior of the RTSM resupply algorithm which they are forecasting for, they generally need to have the same or similar parameters as a number of different RTSM offerings, and rarely if ever can they match the RTSM resupply algorithm accurately. As a result, using known forecasting systems, key supply decisions may be made on improper information (e.g., a forecast that does not match actual trial usage because of algorithmic differences between forecast and management systems), which could lead to wasteful oversupply or stock-outs. Furthermore, because RTSM and clinical trial supply management systems are generally distinct systems, forecasting later stages of the trial while the trial is ongoing is generally performed infrequently (every 1-6 months), and a manual mapping must be performed by the user between the study models in each of those two systems. Reporting in current systems is rigid, and data exploitation can generally only be further performed in external systems like Excel. Most systems are not validated or CFR Part 11-compliant in the sense that clinical trial software usually is, further creating potential mismatches and bad recommendations to be used for key supply decisions.

Forecasting systems generally should consider a number of interrelated variables to model the needed supply over the life of a pharmaceutical trial. For example, the patient visit schedule and dispensing schedule of the drugs must be considered, including any variations on the protocol's schedule of visits that patients might follow over the course of the study. The patient population over time and space should also be considered, including when patients will enroll and where, and how quickly sites will be activated. The forecast should also account for the logistics of the supply network, including issues such as how inventory will get to the sites, how frequently inventory will be shipped, and how long it will take to arrive at trial sites. Inventory constraints should also be accounted for, including country-specific constraints (for example, labelling requirements), per-unit production costs and value, shelf life, and expirations dates of lots.

Resupply algorithms (and forecasters) generally deal with two types of demand: predictable demand and unpredictable demand. Predictable demand encompasses requirements which will be consumed by existing, known patients at any time in the future, where the treatment type and dosage level is known in advance. Unpredictable demand encompasses requirements which will be consumed either by unknown (non-existing) patients ("uncorrelated unpredictable demand"), either by known patients who have not yet had a treatment assigned through randomization, or by known patients who have a general course of treatment assigned but the study design itself includes variability in future dosing ("correlated unpredictable demand").

Competent RTSM forecasters generally deal appropriately with predictable demand, but only the most robust and powerful forecasters can deal with unpredictable demand, which is by its nature unknown in advance. Simulators may yield statistically realistic upper limits on unpredictable demand over some window in time, which result may be used to create safety stock or floor-ceiling buffers (stock placed at sites in advance without knowing if it will be used). Such buffers and settings are generally set manually in a labor-intensive process.

Two time horizons are important to RTSM. The first is sometimes known as the "short window" and is usually equal to or slightly greater than the shipping lead time from a supplying depot into a site in question. For example, buffer or safety stocks can be set to cover for all or almost all anticipated needs within this window of time, and hence prevent stock-outs or missed patient dispensing. Because it may be undesirable to ship replenishment every time a drug is consumed, a second window, sometimes called the "look-ahead window" or "long window," tells the system how long inventory should hold before another shipment is needed. For example, a long window setting might be 30 days.

In some situations, good forecasting tools can stay in sync with good RTSM systems (via regular data feeds) and can continue to provide advice for sponsor companies to set parameter values as described above. In other situations, however, this does not happen. The complexity of many aspects of this process, all centered on deep understanding of resupply algorithms and their parameters, overwhelms many clinical supply professionals (or others responsible for this function).

A supply forecasting system according to the present disclosure may improve upon some or all of the above-noted deficiencies.

Referring now to the drawings, wherein like reference numerals represent the same or similar features in the various views, FIG. 1 is a diagrammatic view of an example system 10 for forecasting and managing a clinical trial, such as a randomized pharmaceutical trial, for example. The system 10 may include a supply forecasting system 12 and a randomization and trial supply management (RTSM) system 14, either or both of which may be in electronic communication with a plurality of user computing devices 16 (one of which is shown in FIG. 1).

Generally, the forecasting system 12 and the RTSM system 14 may be involved in different aspects of planning and administration for a pharmaceutical trial. As will be described in greater detail below, the RTSM system 14 may generally guide and administer the trial, whereas the forecasting system 12 may generate a plan for the trial before complete information for the trial is available, or for a stage of a trial for which complete information is not yet available.

The RTSM system 14 may comprise one or more computing devices and may perform many operations for organizing and orchestrating a pharmaceutical trial, such as patient randomization, blinding, drug dispensing, and automatic drug resupply, in embodiments. The RTSM system 14 may be in electronic communication with one or more user computing devices 16 to receive input from the user (e.g., parameters of a trial) and to provide output to a user (e.g., orders for one or more drugs, a status of a patient participating in the trial, information respective of a trial site, etc.).

The RTSM system 14 may be configured for communication and information exchange with a variety of different user types (that is, communication with one or more user computing devices respective of such user types). For example, in a given trial, the RTSM system 14 may provide an input/output interface for a clinical trial sponsor 18 (e.g., a pharmaceutical company). The trial sponsor 18 may input complete parameters of a clinical trial, or stage thereof, for the RTSM system 14, in embodiments. Such a complete set of parameters may include, for example, patient visits or other actions on patients, lots and operations on lots, inventory and operations on inventory at a site or depot level, shipments and operations on shipments, temperature excursions and their management, return of dispensed or non-dispensed drugs and related approvals and parameter, destruction status of inventory, actions on alerts or notifications, addition and parametrization of sites and depots, countries, setup of forecasting parameters such as a confidence dial and a long window dial, set up of site group enrolment rates, setup of users and their access rights, setup of cohorts, loading of kit and randomization lists, unblinding of a patient or a kit. The RTSM system 14 may then determine and output, to the trial sponsor, which resupply actions may have to be taken. The RTSM system 14 may also track and record the status of the trial based on data from one or more depots, sites, doctors, and patients, as will be described below, and may make such information available to the trial sponsor.

The RTSM system 14 may be in electronic communication with one or more trial sites 20, such as hospitals or clinics, for example. The RTSM system 14 may output instructions to a trial site 20, such as dispensing instructions for particular patients, for example. The RTSM system 14 may also receive data from a trial site 20, such as patient information, dispensing records, and the like, such that the RTSM system 14 has data indicative of which patients took which drugs involved in the trial and which sites, as when.

The RTSM system 14 may further be in communication with one or more distribution facilities 22, such as depots, warehouses, or other facilities involved in the distribution of drug lots and placebos involved in the trial to trial sites 20. The RTSM system 14 may issue shipping instructions to such a facility 22, for example. Such shipping instructions may be generated and/or transmitted automatically by the RTSM system 14, in embodiments, based on a supply plan. The RTSM system may also receive data from such facilities 22, such as shipping records and inventory information, such that the RTSM system 14 has data indicative of distributed inventories of drugs involved in the trial and remaining inventories, and the locations of those inventories.

One or more doctors 24 may also be in electronic communication with the RTSM system 14. The RTSM system 14 may output to such doctors 24 information about the drugs involved in the trial and information about the trial to enable the doctor to inform patients about the trial as appropriate. The RTSM system 14 may receive from such doctors enrollment information (e.g., the number of patients that the doctor has recommended for the trial, the characteristics of those patients, the specific patients that have enrolled, etc.), such that the RTSM system 14 has data indicative of enrollment quantities and characteristics of enrolled patients.

The supply forecasting system 12 may include a processor 28 and a non-transitory, computer-readable memory 30 including instructions that, when executed by the processor 28, cause the processor 28 to perform one or more methods, algorithms, processes, etc. of this disclosure. The memory 30 may store one or more modules in the form of executable instructions (e.g., software) for execution by the processor 28. Example modules are described below.

The memory 30 may store a supply planning module 32, in embodiments. Based on the supply planning module 32, the supply forecasting system may generally generate a plan for supplies of the drug under trial and placebos for the trial before complete information for the trial (or a stage of the trial) is available. The supply forecasting system 12 may then output the supply plan for the trial to the trial sponsor 18 to enable the trial sponsor 18 to properly budget for the trial, acquire appropriate sites and logistical channels for the trial, and the like. For such communications, the supply forecasting system 12 may be in electronic communication with one or more user computing devices 16, including user computing devices 16 respective of the trial sponsor 18.

The memory 30 may also store a specification interpretation module 34, in embodiments. A user (e.g., via a user computing device which, as noted above, may be associated with a trial sponsor) may submit, and supply forecasting system 12 may receive, information indicative of parameters of a trial. The specification interpretation module 34 may process and parse the received information to extract and determine the trial parameters. Based on the parameters of the trial received from the user, the supply planning module 32 may generate a supply plan.

The forecasting system 12 may provide an electronic user interface for use by the trial sponsor, one or more trial sites, one or more depots, one or more doctors, and/or one or more patients. For example, in embodiments, the forecasting system 12 may provide an electronic user interface including one or more dials to enable a user to set certain constraints on a supply plan to be calculated by the forecasting system by adjusting the dials. Based on user actuation of such dials or other input means, the supply forecasting system 12 may receive user input, as discussed below.

In some embodiments, the forecasting system 12 may receive from a user a level of confidence at which, for example, the total projected demand (e.g., predictable, correlated unpredictable, uncorrelated unpredictable, etc.) should be supported. In some embodiments, the user may present various different confidence levels, and the forecasting system may calculate a supply plan forecast for each of those confidence levels. In embodiments, the forecasting system may receive numerous confidence levels from the user directed to different trial parameters—for example, a first confidence level for total demand, a second confidence level for correlated unpredictable demand, etc.

The forecasting system may also receive from the user one or more lengths of time for the study. For example, the user may provide a length of the trial, a length of one or more specific phases of the trial, etc. In some embodiments, the user may present various different lengths of time, and the forecasting system may calculate a supply plan forecast for each of those lengths of time.

The supply forecasting system 12 may also be in electronic communication with the RTSM system 14. During a trial, the supply forecasting system 12 may retrieve data respective of the trial from the RTSM system 14. For such information retrieval, the supply forecasting system 12 may communication with the RTSM system 14 via an application programming interface (API) 38 of the RTSM system 14. Based on a plan comparison module 36, the supply forecasting system 12 may compare the retrieved information about the status of the trial to the forecast supply plan and may generate alerts for the trial sponsor when the trial status deviates substantially from the forecast supply plan.

One or both of the RTSM system 14 and the supply forecasting system 12 may be implemented on a Software-as-a-Service (SaaS) basis, in an embodiment. Accordingly, the supply forecasting system and/or RTSM system 14 may be embodied in one or more servers, databases, etc., that are electronically accessible to users through the internet. Additionally or alternatively, one or both of the supply forecasting system 12 and RTSM system 14, or one or more aspects or functions of the supply forecasting system 12 and RTSM system 14, may be implemented on a local server for a trial sponsor, for example, or in local copies stored on user computing devices respective of the trial sponsor, trial sites, depots, etc.

Although the RTSM system 14 and the supply forecasting system 12 are illustrated and described as separate systems, the RTSM system 14 and the supply forecasting system 12, or some functionality thereof, may be implemented in a single system or in common computing resources, in embodiments.

A supply forecasting system according to one or more aspects of the present disclosure may improve upon known supply forecasting methods and systems. First, known supply forecasting systems are generally used to calculate a comprehensive forecast for the entirety of a trial. Such forecasting systems generally require a large amount of information about the trial to enable a comprehensive plan. As a result, known forecasting systems may not provide substantial utility very early in the trial planning process, when relatively little information about the trial may be available, and a large number of assumptions have to be made to use those systems. In contrast, in embodiments, a supply forecasting system according to the present disclosure may be configured to calculate a supply plan, or a portion thereof, based on whatever information is available to the user, and may be further configured to determine and inform the user of specific milestones (e.g., dates, availability of certain information, etc.) that may trigger a re-calculation of the supply plan, or a calculation of an additional aspect of the supply plan, and thus may enable users to make changes to a plan during a trial without expensive trial delays. A supply forecasting system according to the present disclosure may offer a method for the user to convey different levels of information, as it becomes known, in a flexible manner. A supply forecasting system according to the present disclosure may therefore offer more flexible and robust forecasting of a supply plan, enabling improved logistics in executing a pharmaceutical trial, and may enable more accurate prediction of drug requirements, avoiding expensive wastage, anticipating stock-outs or other problematic situations. It may, for example, reduce the overage (drug required to cover the trial beyond the actual patient needs, to cover for uncertainty and supply chain inefficiencies) by 20%.

Second, known forecasting systems are generally separate from RTSM systems, and thus must acquire information from RTSM systems via inefficient file transfer, which generally requires manual user intervention and may include the exchange of more data than is necessary both of which may be less efficient than desired, and which presents the risk of an inaccurate mapping between the data from both systems. In contrast, in embodiments, a supply forecasting system according to the present disclosure may be integrated with the RTSM system via an API exposed by the RTSM system. As a consequence, instead of inefficient file transfer, supply forecasting system may issue requests and commands to the RTSM system via to API to collect the specific information needed by the forecasting system, without requiring manual intervention, thereby improving the functionality and efficiency of a computer-implemented forecasting system. Data mapping may also be mostly automated and becomes less error-prone than via a manual intervention.

Third, as noted above, known supply forecasting system generally require specific types of information to generate a plan. Known forecasting systems also generally require such information in a specific, single form. In contrast, in embodiments, a forecasting system according to the present disclosure may accept aspects of trial information in multiple formats—e.g., one or more text files and one or more spreadsheets—and may process and parse the submitted information to extract and determine trial parameters on which to base a supply plan.

Figure 2:
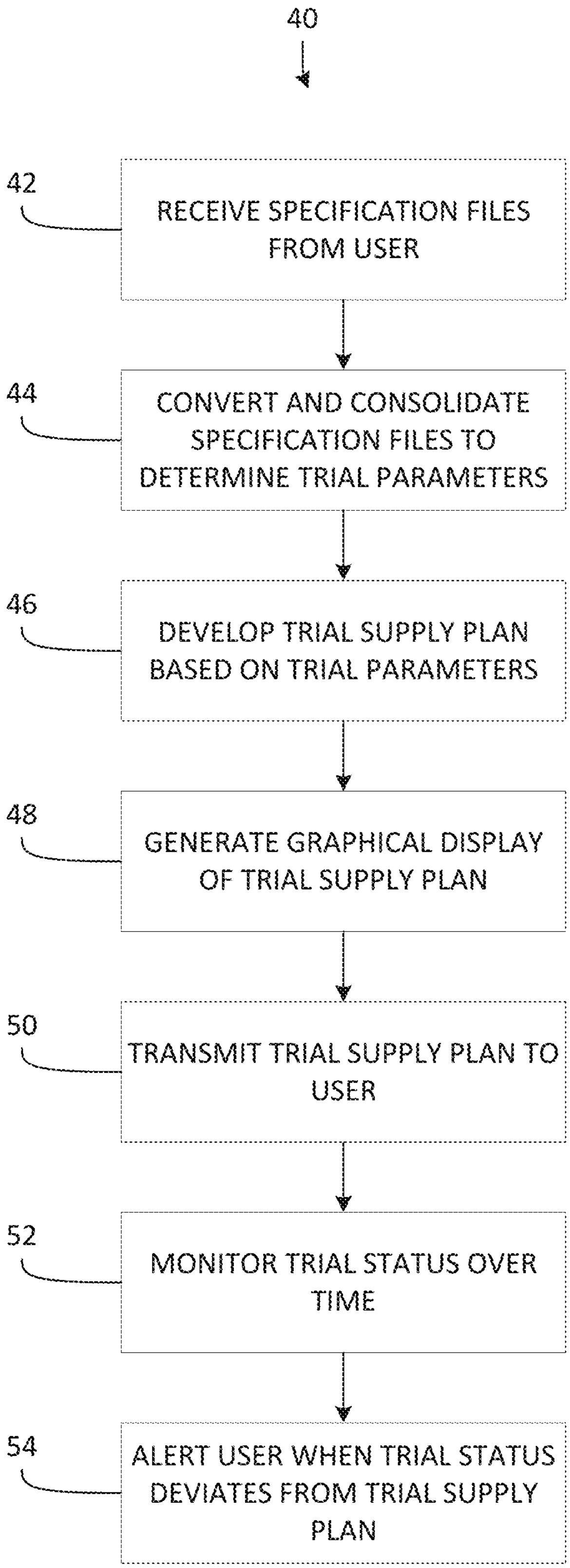
FIG. 2 is a flow chart illustrating an example method of operating a trial supply forecasting system.

FIG. 2 is a flow chart illustrating an example method 40 of operating a trial supply forecasting system. The method 40, or one or more aspects of the method, may be executed by a supply forecasting system, such as the supply forecasting system 12 of FIG. 1, for example. The method 40 of FIG. 2 includes various relatively high-level functions of the trial supply forecasting system. Certain of such functions will be elaborated upon with respect to FIG. 4, FIG. 5, FIG. 6, and FIG. 7.

With continued reference to FIG. 2, the method 40 may include a step 42 that includes receiving one or more specification files from a user. The user may be, for example, a trial sponsor (e.g., a pharmaceutical company). The specification files may include one or more file types. For example, in an embodiment, the specification files may include one or more text files and one or more spreadsheet files. The text may be entered in free or natural form, rather than being responsive to a structured prompt, in embodiments. The specification files may include information available to the sponsor about a proposed pharmaceutical trial, such as a start and duration, a number of desired patients, the rate at which patients are expected to enroll into the study, whether a screening may occur and at which rate this screening fails, a description of the treatment of the patient and in particular any event at which dispensing of drug may occur or the patient may drop or change dose and how those events relate to one another in time and likelihood, a number of sites, a list countries, site groups, regions, depots, a description of the supply network incorporating supply lines and lead times, a description of the different drugs to be tested, the different doses in which they will be tested, drug supply constraints such as expiration, remaining shelf life, maximum lot size or maximum release frequency, etc.

The method 40 may further includes a step 44 that includes converting and consolidating the specification files to extract or otherwise determine parameters of a trial that are included in the specification files. An example method for performing step 44 will be described with respect to FIG. 4 and FIG. 5.

The method 40 may further include a step 46 that includes developing a trial supply plan based on the trial parameters determined from the specification documents. An example method for performing step 46 will be described with respect to FIG. 5. One or more trial supply plans may be determined at step 46. For example, multiple trial supply plans may be determined for different confidence levels associated with the duration of the trial, or different confidence levels associated with the number of patients needed for the trial, or different numbers of doses to be tested in the trial, etc.

Figure 3A:
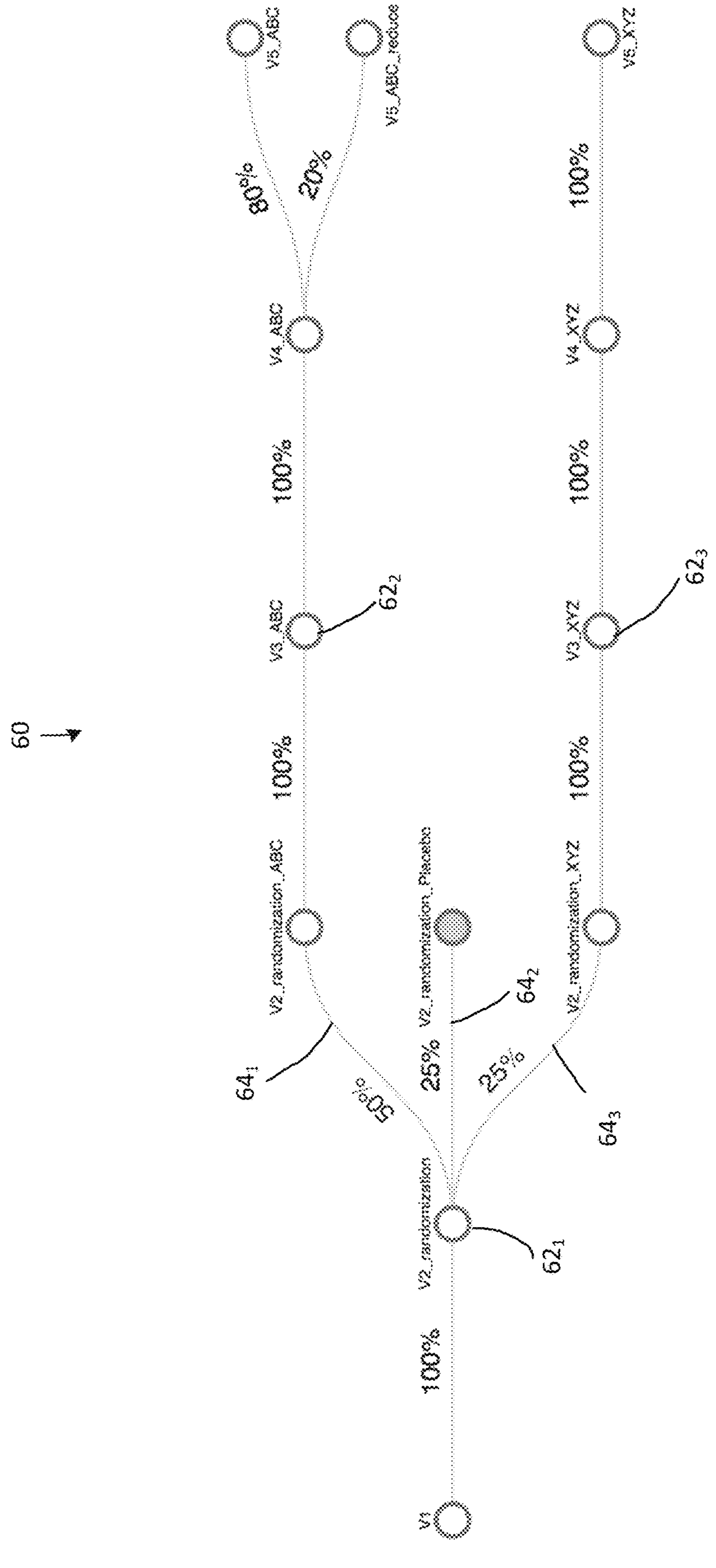
FIG. 3A and FIG. 3B are example graphical displays of an example trial supply plan.
Figure 3B:
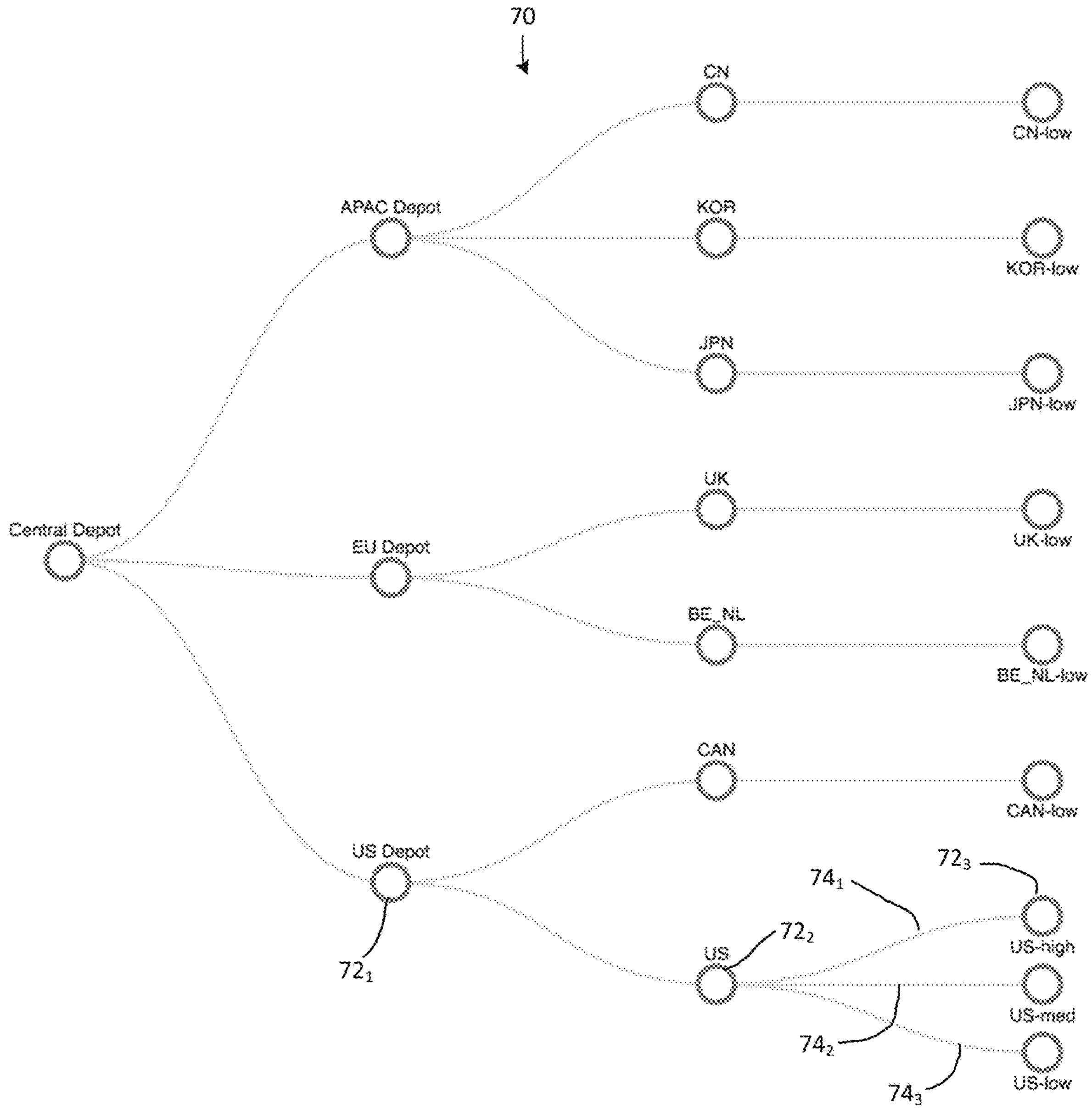

The method 40 may further include a step 48 that includes generating one or more graphical representations of the trial supply plan and the input used to calculate it. FIG. 3A and FIG. 3B are example graphical representations 60, 70 of a trial supply plan or the input used to calculate it. Referring to FIG. 3A, a first graphical representation 60 may include a plurality of nodes 62 (three nodes $\mathbf{62_1}$, $\mathbf{62_2}$, $\mathbf{62_3}$ are indicated in FIG. 3A; for clarity of illustration, not all nodes 62 are indicated), with each node 62 representative of an action in the trial of which the graphical representation 60 is representative, such as a randomization of a trial population, a dispensing of a drug, etc. The graphical representation may further include one or more branches 64 extending from each node. Each branch 64 may illustrate a result of the action of the node 62 from which the branch 64 extends. For example, three branches $64_1$, $64_2$, $64_3$ may extend from an initial node $62_1$ representative of randomizing a patient population, with a first branch $64_1$ indicating an assignment of fifty percent (50%) of the randomized patient population to the ABC portion of the trial, a second branch $64_2$ indicating that twenty-five percent (25%) of the patient population will be included in a placebo portion of the trial, and a third branch $64_3$ indicating that twenty-five percent (25%) of the patient population will be included in the XYZ portion of the trial.

Referring to FIG. 3B, a second graphical representation 70 may include a plurality of nodes 72 (three nodes $72_1$, $72_2$, $72_3$ are indicated in FIG. 3B; for clarity of illustration, not all nodes 72 are indicated), with each node 72 representative of a location, or collection of locations, in the trial, such as a depot, a trial site, or other facility involved in the. For example, a first node $72_1$ is representative of a depot for the US (which may also service Canada), a second node $72_2$ is representative of the US trial population, and a third node $72_3$ is representative of a low-dosage US trial population. The graphical representation may further include one or more branches 74 extending from each node 72. Each branch 74 may illustrate a distribution channel for a sub-portion of the drug included in the node 72 from which the branch 74 extends. For example, three branches $74_1$, $74_2$, $74_3$ may extend from the US trial population node $72_2$ representative of a patient population, with a first branch $74_1$ indicating that a portion of the supply designated for the US trial population will go to the low dosage US trial population $72_3$, a second branch $74_2$ indicating that a portion of the supply designated for the US trial population will go to a medium dosage US trial population, and a third branch $74_3$ indicating that a portion of the supply designated for the US trial population will go to a high dosage US trial population.

Referring again to FIG. 2, the method 40 may further include a step 50 that includes transmitting the trial supply plan to the user. Transmitting the supply plan to the user may include transmitting data comprising one or more graphical representations of the supply plan to a user computing device for display on the user computing device. Transmitting the supply plan to the user may additionally or alternatively include transmitting a table or textual form of the supply plan to the user, and/or some other form of the supply plan, or one or more portions thereof. The transmission may be in the form of a hosted webpage delivered to a user computing device, for example. Additionally or alternatively, the transmission may be in the form of an email or other electronic form, such as downloadable electronic files.

The method 40 may further include a step 52 that includes, after the trial has begun, monitoring the trial status over time. Monitoring the trial status may include periodically, automatically retrieving data respective of the trial from an RTSM system and comparing that data to the trial plan. Any or all aspects of the trial may be compared to the supply plan forecast in step 52. For example, an inventory of the drug under trial at each testing site may be compared to the supply plan forecast to determine if the order schedule should be or must be altered, or if the distribution schedule should or must be altered, to ensure that each testing site is provided with sufficient stock to provide to its testing patients.

The method 40 may further include a step 54 that includes alerting the user when the trial status deviates from the trial supply plan. Examples of, and further details of, steps 52 and 54 will be described with respect to FIG. 7.

Figure 4:
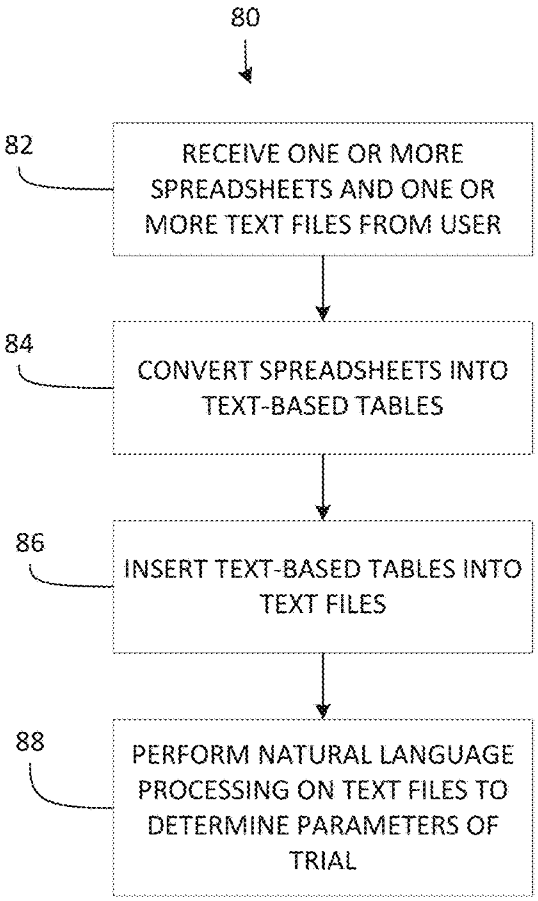
FIG. 4 is a flow chart illustrating an example method of determining parameters of a proposed pharmaceutical trial.

FIG. 4 is a flow chart illustrating an example method 80 of determining parameters of a proposed pharmaceutical trial. The method 80, or one or more aspects of the method 80, may be executed by a supply forecasting system, such as the supply forecasting system 12 of FIG. 1, for example.

The method 80 may include a step 82 that includes receiving a spreadsheet file and one or more text files from the user. The files may include the information about a study to be conducted that is available to the user at the time. The text files may be HTML files, for example. The spreadsheet and text files may be received via a file upload through a website provided by the supply forecasting system, for example. In embodiments, the supply forecasting system may provide an interface in which a user may enter freeform text to describe the proposed study (which entered freeform text may be or may become the one or more text files of step 82), and further upload one or more spreadsheets through the interface.

The method 80 may further include a step 84 that includes converting the spreadsheet into one or more text-based tables. The spreadsheet may be converted into one or more HTML-based tables, for example, or into whatever format the text-based files were provided in, in embodiments.

The method 80 may further include a step 86 that includes inserting the text-based tables into the one or more text files, and a step 88 that includes performing natural language processing on the one or more text files to determine the parameters of the trial. Examples of the natural language processing that may be performed at step 88 will be described with respect to FIG. 5. Further detail on natural language processing is provided in US 20170154168 entitled "Generating RTSM Systems for Clinical Trials" by inventor Edward A. Tourtellotte and assigned to 4G Clinical, LLC which is hereby incorporated by reference in its entirety. Through the use of natural language processing (NLP), users can describe their trial in plain English, independently from the level of detail of information available, and the forecasting system can determine the available details of the trial for further processing.

Figure 5:
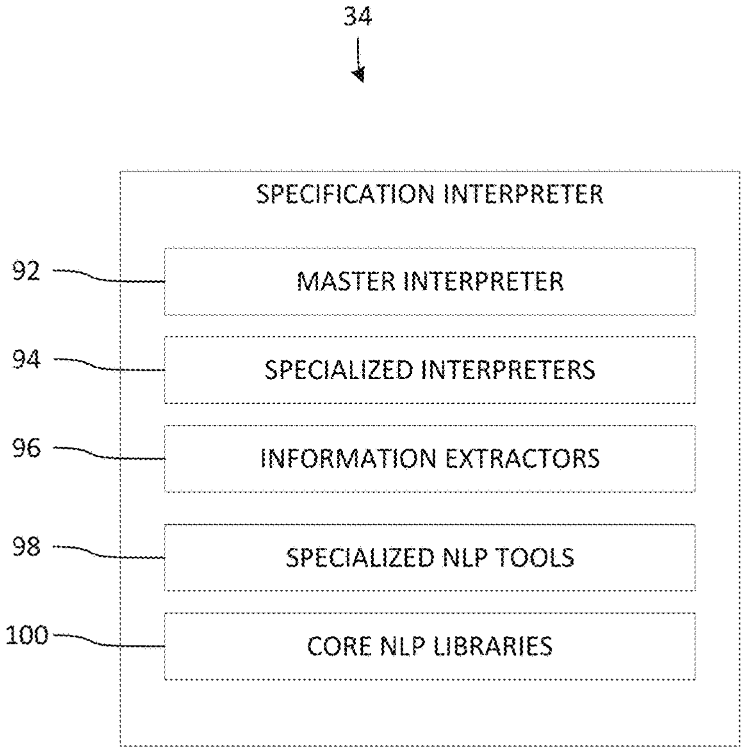
FIG. 5 is a diagrammatic view of an example electronic specification interpreter that applies natural language processing.

FIG. 5 is a diagrammatic view of an example electronic specification interpreter 34 that applies natural language processing. The specification interpreter 34 may perform the method 80 of FIG. 4, and in particular step 88, in embodiments. The specification interpreter 34 may include a master interpreter 92, one or more specialized interpreters 94, one or more information extractors 96, one or more specialized natural language processing (NLP) tools 98, and one or more core NLP libraries 100. The specification interpreter 34 can further include additional components, in embodiments.

A core NLP library, such as the core NLP libraries 100, can include information of a natural language (e.g., English), such as vocabulary and syntax, corpora, taggers, tokenizers, stemmers, lemmatizers, learning algorithms and more. The core NLP library 100 can be used by the specification interpreter 34 to examine the specification entered by a specification writer. For example, the specification interpreter 34 can rely on the core NLP library 100 to recognize words and stems, flag incorrect spelling, analyze grammar and meaning, detect logical operations and data definitions, and/or suggest alternative terms. In some situations, the core NLP library 100 can be provided by a third party, such as from certain programming language (e.g., Java or Python) development toolkits (e.g., Natural Language Tool Kit or NLTK).

A specialized NLP tool, such as the specialized NLP tools 98, can provide system-specific extensions to the core NLP library 100. For example, the specialized NLP tools 98 can include additional information for words, phrases, terms, syntax, reserved words/phrases, keywords, and operators, for example as may be commonly used in the context of certain fields (e.g., clinical trials). The specialized NLP tool 98 can also include advanced language analysis functionality, such as tokenizing, stemming, grammar, collocations, language corpus, sentence structure and meaning analysis, among other natural language processing features. The specialized NLP tools 98 can also include artificial neural networks.

The specialized NLP tools 98 can also be used by the specification interpreter 34 to examine the specification entered by a specification writer. For example, the specification interpreter 34 can rely on the specialized NLP tools 98 to recognize system-specific words, flag incorrect spelling, and/or suggest alternative terms. The specialized NLP tools 98 can be provided by a third party or internally developed. An information extractor, such as the information extractors 96, can extract certain information from the specification. One type of information extracted can include matrices (e.g., information structured in a tabular manner). A matrix may be used in specification development when it is more convenient to organize data in matrix form than in natural language. For example, a matrix can be used to define patient visit schedules and associated dosing regimens or other visit events; a matrix can also be used to define patient kit types, supply chain relationships and lead times, or any other data which is naturally defined in a matrix.

Another type of information extracted can include certain style of sentences such as definitions. A definition could for example be structured as [SUBJECT OF DEFINITION] [VERB PROPOSITION] [ITEM or LIST OF ITEMS], but structure could differ or be made more flexible to enable use of free English style in writing and yet extracting relevant information. Other styles of sentences can be defined as necessary.

The master interpreter 92 can receive a trial specification. The master interpreter 92 can perform top level analysis of the specification and can organize interpretation in a logical sequence of themes. A theme can include one or more defined trial topics, which can run across one or more sections of the specification document. A particular theme of the interpretation can correspond to a specialized interpreter 94, configured to analyze information relevant to the particular theme across the specification document (in one or more sections). The master interpreter 92 can invoke different specialized interpreters to process different themes of the trial through the specification.

The specialized interpreters 94 can include a study level interpreter, a randomization interpreter, an action interpreter, a drug supply interpreter, a manufacturing interpreter, an enrollment interpreter or other interpreters as required. A study level interpreter can interpret the high-level information in the specification. For example, high level information can include certain study level information, such as the total number of patients desired to be screened and randomized, the randomization scheme and method, and other required parameters. A randomization interpreter can interpret randomization information in the specification. An action interpreter can interpret event actions information in the specification. For example, an event action can include information such as what drug dispensing may occur within the context of each patient visit. A drug supply interpreter can interpret the drug supply information in the specification. For example, the drug supply information can include supply network, shipping rules, dispensing kits info, etc. A manufacturing interpreter may interpret the various production steps and intermediate manufacturing lead time to transform the investigational substance into kits dispensable to patients. An enrollment interpreter may interpret the rate at which patients will enter the study at various levels (e.g. study-level, region-level, etc.). The list of specialized interpreters is not exhaustive. Additional specialized interpreters can be added when needed.

In some situations, the master interpreter 92 can be an entry point into the specification interpreter 34. For example, the master interpreter 92 can receive a specification and divide the interpretation into different sections or themes. The master interpreter 92 can then invoke an appropriate specialized interpreter 94 to analyze each section or theme. Each specialized interpreter 94 can invoke one or more information extractors 96, as needed, to extract information from each section or theme of the specification, such as matrices and definitions. Each information extractor 96 can invoke one or more specialized NLP tools 98, as needed. Each specialized NLP tool 98 can then invoke one or more core NLP libraries 100 to assist processing each section or theme of the specification.

The output result of a core NLP library 100 can be returned to the specialized NLP tool 98 that invokes the core NLP library 100. The output result of a specialized NLP tool 98 can be returned to the information extractor 96 that invokes the specialized NLP library 100. The output result of an information extractor 96 can be returned to the specialized interpreter 94 that invokes the information extractor 96. The output result of a specialized interpreter 94 can be returned to the master interpreter 92 that invokes the specialized interpreter 94.

In some embodiments, the output of the specification interpreter 34 can include basic data structures and driving logic. The basic data structures and driving logic can include logic containers and other necessary or related structures. For example, the data structures may hold planned patient visit and dosing information, data driving information (e.g. BMI for use in dosing), data related to supply chain organization, supply shipments and/or patient kits, or any other data which is desired to be collected or acted upon during the trial. Where necessary, logic containers can hold specific processing instructions for the forecasting system in order to comply with the specification.

Figure 6:
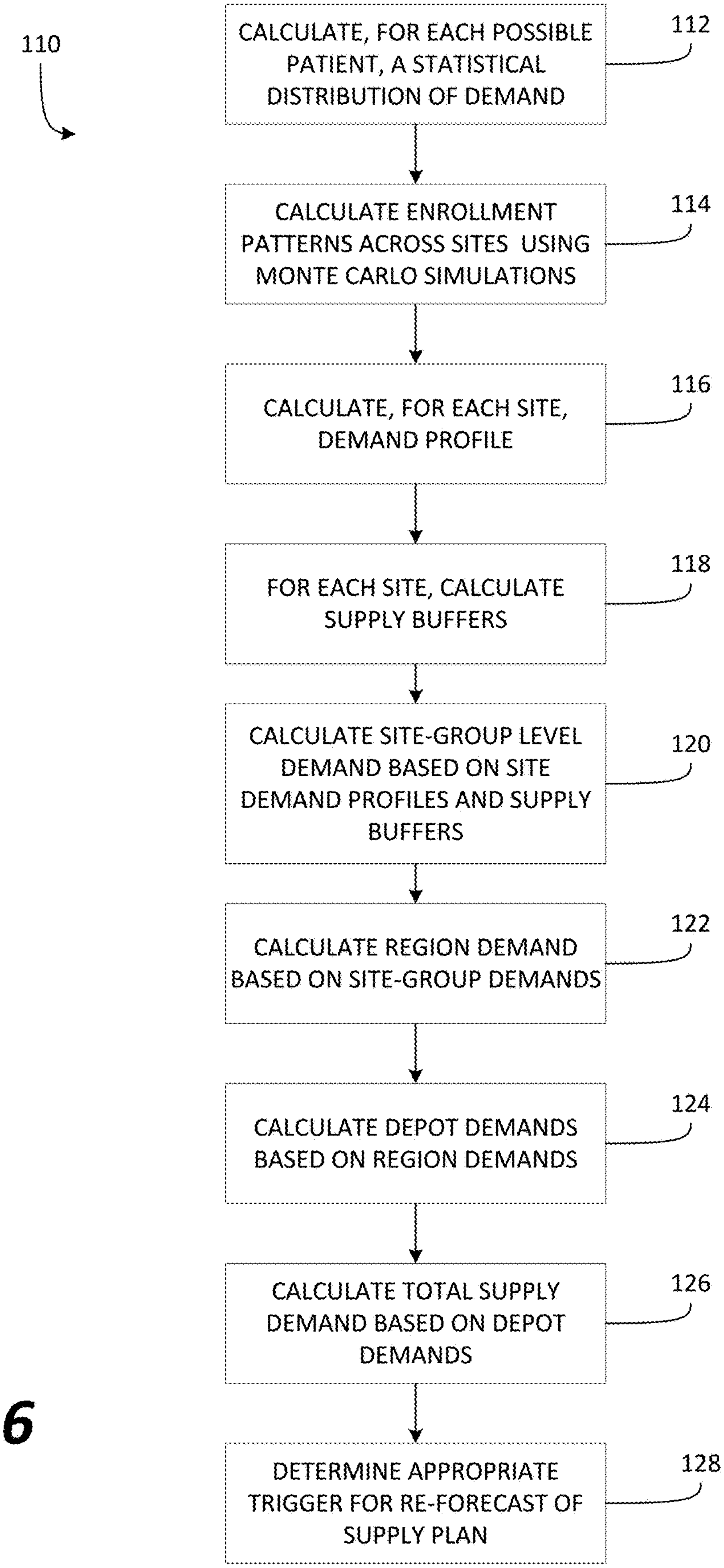
FIG. 6 is a flow chart illustrating an example method of determining a trial supply forecast.

FIG. 6 is a flow chart illustrating an example method 110 of determining a trial supply forecast. The method 110, or one or more aspects of the method 110, may be executed by a supply forecasting system, such as the supply forecasting system 12 of FIG. 1, for example.

The method 110 may include a step 112 that includes calculating, for each of a plurality of hypothetical patients, a statistical distribution of demand. A demand may include the quantity of a drug, a drug dose, and/or a placebo needed for one or more points in time during the patient's treatment. The distribution of demand may be a discrete distribution driven by the randomization ratios, for example. In other embodiments, other statistical distribution types may be used to determine patient demand. The result of the patient demand calculation step may be a time series for which each point expands the likelihood for the demand, cumulatively or for a given period of time, to be of a certain amount. For example, after 1 month, the cumulative demand for a new patient in kit type KT-12 mg may be of 0 with 40% chance, 1 with 30% chance, 2 with 25% chance, and 3 with 5% chance.

The method 110 may further include a step 114 that includes calculating enrollment patterns across sites. Site enrolment patterns may be calculated based on Monte Carlo simulations, in embodiments. A result of the simulating enrollment step may be a most-likely set of patient quantities that would enroll at each of a plurality of testing sites.

The method 110 may further include a step 116 that includes calculating, for each site, a supply demand profile, based on the simulated enrollment patterns and the per-patient demand profiles. That is, assuming a patient accrual rate that may be represented as a Poisson distribution as estimated above, and based on the patient-level distribution, step 116 may include calculating a compound statistical distribution of the demand for all patients susceptible to enroll in each particular site.

The method 110 may further include a step 118 that includes calculating, for each site, supply buffers. The supply buffers may be calculated according to user input, in embodiments. For example, as noted above, the user may actuate one or more dials to set a confidence rating. The lower the user sets the confidence rating, the higher the supply buffers may be set, and vice-versa.

The method 110 may further include a step 120 that includes calculating site-group level demand based on the site demand profiles and supply buffers. A site-group level demand may include, for example, a demand for each supply type (e.g., one or more drug doses and a placebo) at each testing site. In an embodiment, the site-specific buffers may be added to the demands calculated for each site to determine the group-level demand.

The method 110 may further include a step 122 that includes calculating region demands based on site-group demands, a step 124 that includes calculating depot demands based on region demands, and a step 126 calculating a total supply demand based on depot demands. Steps 122, 124, and 126 may include simple arithmetic as well as statistical computations, in embodiments—e.g., adding the demands for each site-group in a region to determine the total demand for that region, adding the demands for each region serviced by a particular depot to determine the total demand for that depot, and so on, either in terms of expected value or in terms of statistical distributions.

The method 110 may further include a step 128 that includes determining an appropriate manufacturing/packaging timing and quantities over the course of the study, as well as a trigger for calculating a re-forecast of the supply plan. This may be one of, or a combination of, a minimum frequency, a calculation based on expiry dating, external constraints provided by the user such as drug availability, and may rely on operations research techniques such as Constraint Programming, Neural Networks, Mixed Integer Programming, etc.

Figure 7:
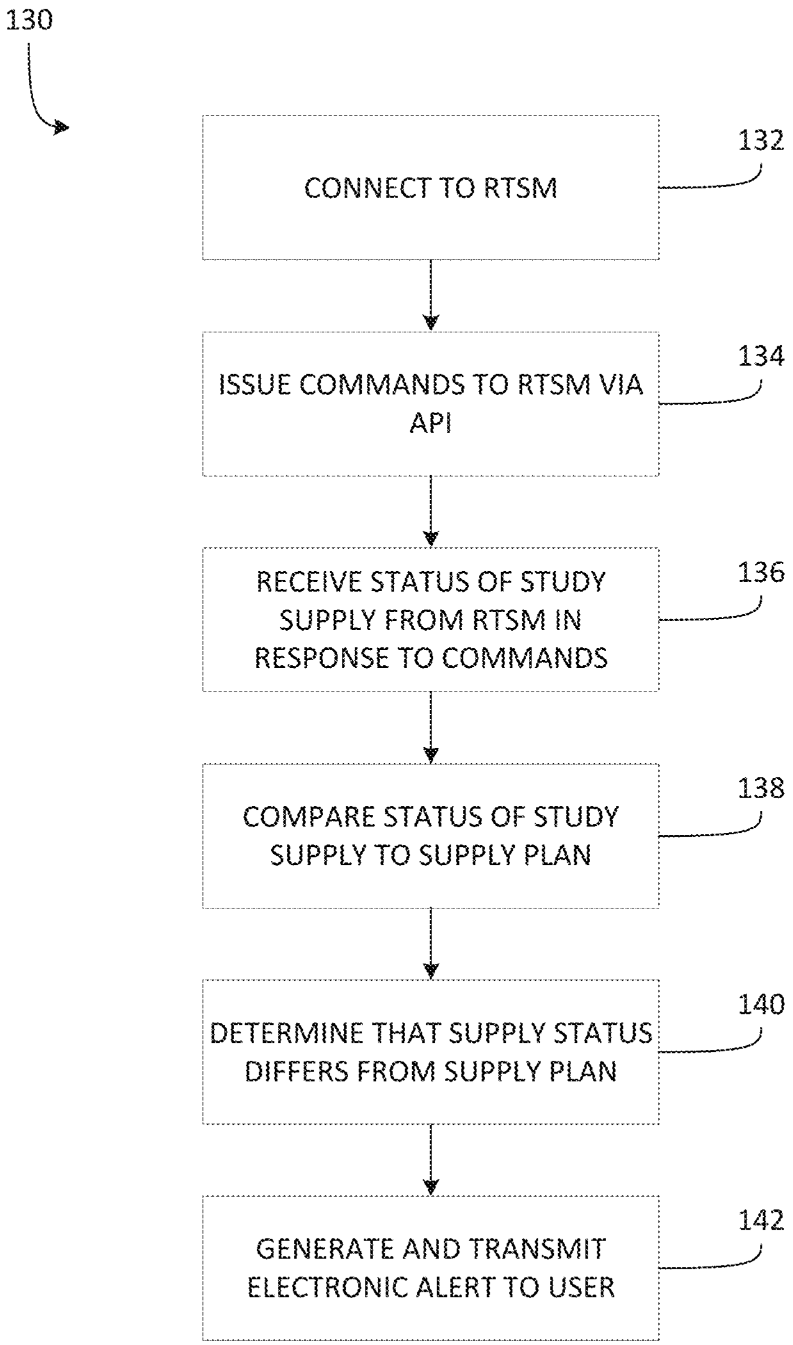
FIG. 7 is a flow chart illustrating an example method of monitoring a trial with respect to a supply forecast for that trial.

FIG. 7 is a flow chart illustrating an example method 130 of monitoring a trial with respect to a supply forecast for that trial. The method, or one or more aspects of the method, may be executed by a supply forecasting system, such as the supply forecasting system 12 of FIG. 1, for example.

The method 130 may include a step 132 that includes connecting (e.g., electronically) to an RTSM system and a step 134 that includes issuing one or more commands to the RTSM system via an API exposed by the RTSM system. The commands may request specific data types, and may remove the need for the RTSM system to exchange whole files with the forecasting system, thereby improving the efficiency of the RTSM system and the forecasting system. The commands may request a number of patients enrolled at one or more sites or in one or more groups, regions, etc. The commands may additionally or alternatively request an inventory of available supply at one or more sites, depots, etc. The commands may additionally or alternatively request records of patient doses, patient information, or any other information related to the status of the trial.

The method 130 may further include a step 136 that includes receiving the status of the supply of one or more drugs in the study in response to the commands issued in step 134. As noted above, due to the use of the RTSM system API, the status information may be provided to the forecasting system by the RTSM system without the use of whole file exchange, and instead the requested data may be directly transmitted and received without the need for packaging that data as one or more files, and without the need for use manual selection of or opening of such files.

The method 130 may further include a step 138 that includes comparing the status of the study supply to a previously-calculated supply plan respective of the study. As discussed above, the forecasting system may compare any or all aspects of the study in progress—inventory levels in one or more depots or at one or more sites, enrollment at one or more sites, etc. —to a supply plan previously calculated by the forecasting system, which forecast supply plan may be been used by the study sponsor for logistical and financial commitments for the study.

The method 130 may further include a step 140 that includes determining that the trial supply status differs from the supply plan. The trial status may be determined to differ from the supply plan when the difference between the trial status and the supply plan may result in a stock-out at a site or a depot, for example, or will result in an inability to complete the trial in the desired amount of time due to low enrollment at one or more sites, in another example. Step 140 may include determining that the trial supply differs from the supply plan forecast when the difference is greater than a threshold percentage, such as a few percent (e.g., five percent (5%)), for example. Of course, any appropriate threshold percentage may be used.

The method 130 may further include a step 142 that includes generating and transmitting an electronic alert to the user in response to determining that the trial supply status differs from the supply plan. The electronic alert may be transmitted via email, text message, or other message, in embodiments. For example, in an embodiment in which the forecasting system provides an electronically-accessible interface, the alert may be sent to a user account associated with a user of that interface, for the user to review upon access of the interface. The alert may include, for example, a notification that the trial status has deviated from the forecasted plan. The alert may additionally or alternatively include corrective action, such as a correction to one or more shipments to one or more sites, a correction to the manufacturing quantity of one or more supplies, a correction to the enrolment cap at one or more sites, etc. In an embodiment, the forecasting system may automatically generate a document, such as an order, a shipment instruction, or an instruction to a trial site, and include the automatically generated document in the alert, that a user of the forecasting system can then cause to be transmitted if desired to effect corrective action.

Figure 8:
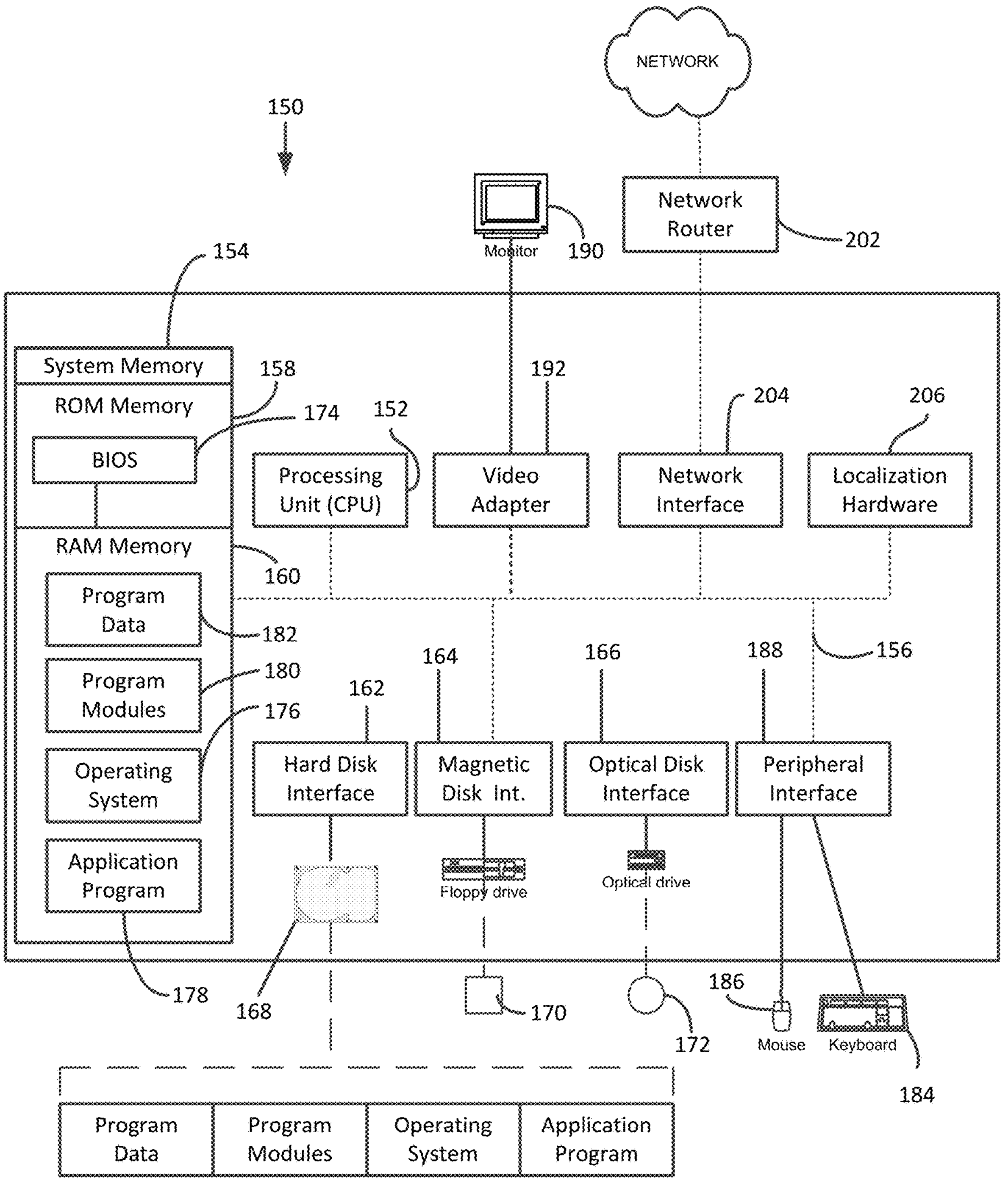
FIG. 8 is a diagrammatic view of an illustrative computing system that includes a general purpose computing system environment.

FIG. 8 is a diagrammatic view of an illustrative computing system that includes a general purpose computing system environment 150, such as a desktop computer, laptop, smartphone, tablet, or any other such device having the ability to execute instructions, such as those stored within a non-transient, computer-readable medium. Furthermore, while described and illustrated in the context of a single computing system 150, those skilled in the art will also appreciate that the various tasks described hereinafter may be practiced in a distributed environment having multiple computing systems 150 linked via a local or wide-area network in which the executable instructions may be associated with and/or executed by one or more of multiple computing systems 150. The computing environment, or portions thereof, may comprise one or more of the supply forecasting system 12, the RTSM system 14, and one or more user computing devices 16 of FIG. 1.

With continued reference to FIG. 8, in its most basic configuration, the computing system environment 150 typically includes at least one processing unit 152 and at least one memory 154, which may be linked via a bus 156. Depending on the exact configuration and type of computing system environment, the computer readable memory 154 may be volatile (such as RAM 160), non-volatile (such as ROM 158, flash memory, etc.) or some combination of the two. Computing system environment 150 may have additional features and/or functionality. For example, computing system environment 150 may also include additional storage (removable and/or non-removable) including, but not limited to, magnetic or optical disks, tape drives and/or flash drives. Such additional memory devices may be made accessible to the computing system environment 150 by means of, for example, a hard disk drive interface 162, a magnetic disk drive interface 164, and/or an optical disk drive interface 166. As will be understood, these devices, which would be linked to the system bus 156, respectively, allow for reading from and writing to a hard disk 168, reading from or writing to a removable magnetic disk 170, and/or for reading from or writing to a removable optical disk 172, such as a CD/DVD ROM or other optical media. The drive interfaces and their associated computer-readable media allow for the nonvolatile storage of computer readable instructions, data structures, program modules and other data for the computing system environment 150. Those skilled in the art will further appreciate that other types of computer readable media that can store data may be used for this same purpose. Examples of such media devices include, but are not limited to, magnetic cassettes, flash memory cards, digital videodisks, Bernoulli cartridges, random access memories, nano-drives, memory sticks, other read/write and/or read-only memories and/or any other method or technology for storage of information such as computer readable instructions, data structures, program modules or other data. Any such computer storage media may be part of computing system environment 150.

A number of program modules may be stored in one or more of the memory/media devices. For example, a basic input/output system (BIOS) 174, containing the basic routines that help to transfer information between elements within the computing system environment 150, such as during start-up, may be stored in ROM 158. Similarly, RAM 160, hard drive 168, and/or peripheral memory devices may be used to store computer executable instructions comprising an operating system 176, one or more applications programs 178 (such as a Web browser and/or other applications that execute the methods and processes of this disclosure), other program modules 180, and/or program data 182. Still further, computer-executable instructions may be downloaded to the computing environment 150 as needed, for example, via a network connection.

An end-user may enter commands and information into the computing system environment 150 through input devices such as a keyboard 184 and/or a pointing device 186. While not illustrated, other input devices may include a microphone, a joystick, a game pad, a scanner, etc. These and other input devices would typically be connected to the processing unit 152 by means of a peripheral interface 188 which, in turn, would be coupled to bus 156. Input devices may be directly or indirectly connected to processor 152 via interfaces such as, for example, a parallel port, game port, firewire, or a universal serial bus (USB). To view information from the computing system environment 150, a monitor 190 or other type of display device may also be connected to bus 156 via an interface, such as via video adapter 192. In addition to the monitor 190, the computing system environment 150 may also include other peripheral output devices, not shown, such as speakers and printers.

The computing system environment 150 may also utilize logical connections to one or more computing system environments. Communications between the computing system environment 150 and the remote computing system environment may be exchanged via a further processing device, such a network router 202, that is responsible for network routing. Communications with the network router 202 may be performed via a network interface component 204. Thus, within such a networked environment, e.g., the Internet, World Wide Web, LAN, or other like type of wired or wireless network, it will be appreciated that program modules depicted relative to the computing system environment 150, or portions thereof, may be stored in the memory storage device(s) of the computing system environment 150.

The computing system environment 150 may also include localization hardware 206 for determining a location of the computing system environment 150. In embodiments, the localization hardware 206 may include, for example only, a GPS antenna, an RFID chip or reader, a WiFi antenna, or other computing hardware that may be used to capture or transmit signals that may be used to determine the location of the computing system environment 150.

While this disclosure has described certain embodiments, it will be understood that the claims are not intended to be limited to these embodiments except as explicitly recited in the claims. On the contrary, the instant disclosure is intended to cover alternatives, modifications and equivalents, which may be included within the spirit and scope of the disclosure. Furthermore, in the detailed description of the present disclosure, numerous specific details are set forth in order to provide a thorough understanding of the disclosed embodiments. However, it will be obvious to one of ordinary skill in the art that systems and methods consistent with this disclosure may be practiced without these specific details. In other instances, well known methods, procedures, components, and circuits have not been described in detail as not to unnecessarily obscure various aspects of the present disclosure.

Some portions of the detailed descriptions of this disclosure have been presented in terms of procedures, logic blocks, processing, and other symbolic representations of operations on data bits within a computer or digital system memory. These descriptions and representations are the means used by those skilled in the data processing arts to most effectively convey the substance of their work to others skilled in the art. A procedure, logic block, process, etc., is herein, and generally, conceived to be a self-consistent sequence of steps or instructions leading to a desired result. The steps are those requiring physical manipulations of physical quantities. Usually, though not necessarily, these physical manipulations take the form of electrical or magnetic data capable of being stored, transferred, combined, compared, and otherwise manipulated in a computer system or similar electronic computing device. For reasons of convenience, and with reference to common usage, such data is referred to as bits, values, elements, symbols, characters, terms, numbers, or the like, with reference to various embodiments of the present invention.

It should be borne in mind, however, that these terms are to be interpreted as referencing physical manipulations and quantities and are merely convenient labels that should be interpreted further in view of terms commonly used in the art. Unless specifically stated otherwise, as apparent from the discussion herein, it is understood that throughout discussions of the present embodiment, discussions utilizing terms such as "determining" or "outputting" or "transmitting" or "recording" or "locating" or "storing" or "displaying" or "receiving" or "recognizing" or "utilizing" or "generating" or "providing" or "accessing" or "checking" or "notifying" or "delivering" or the like, refer to the action and processes of a computer system, or similar electronic computing device, that manipulates and transforms data. The data is represented as physical (electronic) quantities within the computer system's registers and memories and is transformed into other data similarly represented as physical quantities within the computer system memories or registers, or other such information storage, transmission, or display devices as described herein or otherwise understood to one of ordinary skill in the art.

What is claimed is:

1. A computer-implemented method of generating an alert for a clinical trial based at least in part on analysis of a plurality of characteristics of the clinical trial, the characteristics comprising a quantity of patients, a plurality of sites, and two or more confidence values, the method comprising:

performing, with at least one processor, natural language processing (NLP) on a combination of tabularly structured data and free text to identify one or more of the characteristics of the clinical trial;

calculating, with the at least one processor and according to the plurality of characteristics, a plurality of demand profiles for a clinical supply for the plurality of sites;

calculating, with the at least one processor and according to the two or more confidence values, a plurality of buffer quantities of the clinical supply for the plurality of sites, wherein the plurality of buffer quantities includes a first buffer quantity of the clinical supply for a first site of the plurality of sites, wherein the two or more confidence values comprise a first confidence value with respect to correlated unpredictable demand for the clinical supply and a second confidence value with respect to uncorrelated unpredictable demand for the clinical supply, wherein the first confidence value indicates a probability that the first buffer quantity is sufficient to provide the clinical supply to enrolled patients with uncertain future courses of treatment at the first site, and wherein the second confidence value indicates a probability that the first buffer quantity is sufficient to provide the clinical supply to future patients who have not yet enrolled at the first site;

calculating, with the at least one processor, a supply plan for the clinical trial according to the plurality of demand profiles for the clinical supply and the plurality of buffer quantities for the clinical supply for the plurality of sites;

with the at least one processor, establishing electronic communication with an RTSM system and outputting commands to the RTSM system via an application programming interface (API) of the RTSM system, to determine a status of the clinical trial; and based on a difference between the supply plan and the status of the clinical trial, generating and transmitting the alert recommending a corrective action.

2. The method of claim 1, wherein calculating the plurality of demand profiles for the clinical supply for the plurality of sites comprises:

for each respective site of the plurality of sites, calculating, with the at least one processor, a respective statistical distribution of forecasted demand for the respective site at each of a plurality of time points.

3. The method of claim 2, further comprising:

for each respective site of the plurality of sites, calculating a respective upper limit on the correlated unpredictable demand and a respective upper limit on the uncorrelated unpredictable demand for the clinical supply over a time period, wherein calculating the plurality of buffer quantities of the clinical supply comprises calculating the first buffer quantity based on the first confidence value, the second confidence value, the respective upper limit on the correlated unpredictable demand for the first site, the respective upper limit on the uncorrelated unpredictable demand for the first site, and the respective statistical distribution of forecasted demand for the first site.

4. The method of claim 2, further comprising, for each respective site of the plurality of sites, calculating a second respective demand profile for a second clinical supply, wherein calculating the second respective demand profile for the second clinical supply for the respective site comprises calculating a second respective statistical distribution of forecasted demand for the second clinical supply for the clinical trial and for the respective site.

5. The method of claim 2, wherein calculating the respective statistical distribution of forecasted demand for the clinical supply for the respective site comprises calculating a forecasted demand for a drug, drug dose, and/or placebo for the clinical trial and for the respective site.

6. The method of claim 5, wherein calculating the plurality of demand profiles for the clinical supply comprises, for each respective site of the plurality of sites, calculating a respective demand profile for the clinical supply for the respective site, including:

forecasting patient enrollment over time at the respective site;

forecasting a per-patient demand for the clinical supply over time for each patient of a plurality of projected patients; and determining the respective statistical distribution of forecasted demand for the clinical supply at the respective site based at least in part on the forecasted patient enrollment at the respective site and the forecasted per-patient demand for the clinical supply over time.

7. The method of claim 1, wherein calculating the supply plan comprises:

determining, with the at least one processor, a respective uncertainty value at each of a plurality of points in time; and calculating, with the at least one processor, according to the respective uncertainty values, a respective forecasted demand quantity for each of the plurality of points in time.

8. The method of claim 1, wherein:

the characteristics of the clinical trial comprise a respective patient enrollment limit for each of the plurality of sites;

the method further comprises calculating, by the at least one processor, for each respective site of the plurality of sites, a respective date on which the respective patient enrollment limit is forecasted to be met; and wherein calculating the plurality of demand profiles for the clinical supply for the plurality of sites comprises calculating each respective demand profile of the plurality of demand profiles corresponding to each respective site of the plurality of sites according to the respective date for the respective site.

9. The method of claim 1, wherein the performing the NLP on the tabularly structured data and the free text comprises performing the NLP on the free text and on information structured in an electronic text-based table.

10. The method of claim 9, wherein performing the NLP on the free text and on the information structured in the electronic text-based table comprises:

receiving the tabularly structured data formatted as a spreadsheet; and transforming the spreadsheet to the electronic text-based table.

11. The method of claim 1, further comprising:

determining the difference between the supply plan and the status of the clinical trial, including comparing, with the at least one processor, the status of the clinical trial to the supply plan.

12. An apparatus comprising:

at least one processor; and at least one storage medium having encoded thereon executable instructions that, when executed by the at least one processor, cause the at least one processor to carry out a method of generating an alert for a clinical trial based at least in part on analysis of a plurality of characteristics of the clinical trial, the characteristics comprising a quantity of patients, a plurality of sites, and two or more confidence values, the method comprising:

performing, with at least one processor, natural language processing (NLP) on a combination of tabularly structured data and free text to identify one or more of the characteristics of the clinical trial;

calculating, with the at least one processor and according to the plurality of characteristics, a plurality of demand profiles for a clinical supply for the plurality of sites;

calculating, with the at least one processor and according to the two or more confidence values, a plurality of buffer quantities of the clinical supply for the plurality of sites, wherein the plurality of buffer quantities includes a first buffer quantity of the clinical supply for a first site of the plurality of sites, wherein the two or more confidence values comprise a first confidence value with respect to correlated unpredictable demand for the clinical supply and a second confidence value with respect to uncorrelated unpredictable demand for the clinical supply, wherein the first confidence value indicates a probability that the first buffer quantity is sufficient to provide the clinical supply to enrolled patients with uncertain future courses of treatment at the first site, and wherein the second confidence value indicates a probability that the first buffer quantity is sufficient to provide the clinical supply to future patients who have not yet enrolled at the first site;

calculating, with the at least one processor, a supply plan for the clinical trial according to the plurality of demand profiles for the clinical supply and the plurality of buffer quantities for the clinical supply for the plurality of sites;

with the at least one processor, establishing electronic communication with an RTSM system and outputting commands to the RTSM system via an application programming interface (API) of the RTSM system, to determine a status of the clinical trial; and based on a difference between the supply plan and the status of the clinical trial, generating and transmitting the alert recommending a corrective action.

13. The apparatus of claim 12, wherein calculating the plurality of demand profiles for the clinical supply for the plurality of sites comprises:

for each respective site of the plurality of sites, calculating, with the at least one processor, a respective statistical distribution of forecasted demand for the respective site at each of a plurality of time points.

14. The apparatus of claim 13, wherein:

the method further comprises, for each respective site of the plurality of sites, calculating a respective upper limit on the correlated unpredictable demand and a respective upper limit on the uncorrelated unpredictable demand for the clinical supply over a time period; and calculating the plurality of buffer quantities of the clinical supply comprises calculating the first buffer quantity based on the first confidence value, the second confidence value, the respective upper limit on the correlated unpredictable demand for the first site, the respective upper limit on the uncorrelated unpredictable demand for the first site, and the respective statistical distribution of forecasted demand for the first site.

15. The apparatus of claim 13, wherein the method further comprises, for each respective site of the plurality of sites, calculating a second respective demand profile for a second clinical supply, wherein calculating the second respective demand profile for the second clinical supply for the respective site comprises calculating a second respective statistical distribution of forecasted demand for the second clinical supply for the clinical trial and for the respective site.

16. The apparatus of claim 13, wherein calculating the respective statistical distribution of forecasted demand for the clinical supply for the respective site comprises calculating a forecasted demand for a drug, drug dose, and/or placebo for the clinical trial and for the respective site.

17. The apparatus of claim 16, wherein calculating the plurality of demand profiles for the clinical supply comprises, for each respective site of the plurality of sites, calculating a respective demand profile for the clinical supply for the respective site, including:

forecasting patient enrollment over time at the respective site;

forecasting a per-patient demand for the clinical supply over time for each patient of a plurality of projected patients; and determining the respective statistical distribution of forecasted demand for the clinical supply at the respective site based at least in part on the forecasted patient enrollment at the respective site and the forecasted per-patient demand for the clinical supply over time.

18. At least one non-transitory computer-readable medium having encoded thereon instructions that, when executed by at least one processor, cause the at least one processor to perform a method of generating an alert for a clinical trial based at least in part on analysis of a plurality of characteristics of the clinical trial, the characteristics comprising a quantity of patients, a plurality of sites, and two or more confidence values, the method comprising:

performing, with at least one processor, natural language processing (NLP) on a combination of tabularly structured data and free text to identify one or more of the characteristics of the clinical trial;

calculating, with the at least one processor and according to the plurality of characteristics, a plurality of demand profiles for a clinical supply for the plurality of sites;

calculating, with the at least one processor and according to the two or more confidence values, a plurality of buffer quantities of the clinical supply for the plurality of sites, wherein the plurality of buffer quantities includes a first buffer quantity of the clinical supply for a first site of the plurality of sites, wherein the two or more confidence values comprise a first confidence value with respect to correlated unpredictable demand for the clinical supply and a second confidence value with respect to uncorrelated unpredictable demand for the clinical supply, wherein the first confidence value indicates a probability that the first buffer quantity is sufficient to provide the clinical supply to enrolled patients with uncertain future courses of treatment at the first site, and wherein the second confidence value indicates a probability that the first buffer quantity is sufficient to provide the clinical supply to future patients who have not yet enrolled at the first site;

calculating, with the at least one processor, a supply plan for the clinical trial according to the plurality of demand profiles for the clinical supply and the plurality of buffer quantities for the clinical supply for the plurality of sites;

with the at least one processor, establishing electronic communication with an RTSM system and outputting commands to the RTSM system via an application programming interface (API) of the RTSM system, to determine a status of the clinical trial; and based on a difference between the supply plan and the status of the clinical trial, generating and transmitting the alert recommending a corrective action.

19. The method of claim 1, further comprising receiving, via a user interface, first input data representing the first confidence value with respect to the correlated unpredictable demand for the clinical supply and second input data representing the second confidence value with respect to the uncorrelated unpredictable demand for the clinical supply, wherein the first confidence value differs from the second confidence value.

20. The method of claim 1, further comprising controlling, with the RTSM system, distribution of the clinical supply based on the supply plan, wherein controlling distribution of the clinical supply based on the supply plan includes generating shipping instructions, transmitting the shipping instructions, issuing the shipping instructions to one or more distribution facilities, and/or providing output identifying one or more resupply actions to be completed by a sponsor of the clinical trial.

* * * * *